United States Patent [19]

Holloway et al.

[11] 3,954,822

[45] May 4, 1976

[54] LEAD SALTS OF DI- OR TRI-NITRORESORCINOL

[75] Inventors: Kenneth John Holloway, Welling; George William Charles Taylor, Waltham Abbey; Arwyn Theophilus Thomas, Orpington, all of England

[73] Assignee: Ministry of Defence, London, England

[22] Filed: Mar. 7, 1967

[21] Appl. No.: 621,367

[30] Foreign Application Priority Data
Mar. 8, 1966 United Kingdom............... 10217/66

[52] U.S. Cl............................... 260/435 A; 149/22; 149/24
[51] Int. Cl.² .......................................... C07F 7/24
[58] Field of Search................... 260/435 A; 149/24

[56] References Cited
UNITED STATES PATENTS
3,238,076   3/1966   Taylor et al. ..................... 149/24 X OTHER PUBLICATIONS
Urbanski, Chemistry and Technology of Explosives, Vol. III, Pergamon Press, New York, 1967, pp. 212 to 215, 220, 221 and 240 to 243.

Primary Examiner—Leland A. Sebastian

[57] ABSTRACT

A new class of primary explosives which are polybasic lead salts of nitro-substituted resorcinols, optionally containing a minor proportion of finely-divided boron dispersed throughout individual crystals; and processes for their manufacture.

4 Claims, No Drawings

LEAD SALTS OF DI- OR TRI-NITRORESORCINOL

The invention relates to primary explosives and compositions thereof which may be used as intitiatory or fast delay explosives in fuses, detonators and the like and which will explode under mild stimulus to produce a detonation wave capable of exploding quantities of less sensitive explosive.

Normal lead trinitroresorcinate (lead styphnate) is a well-known primary explosive which is widely used in priming compositions and the monobasic lead salt of trinitroresorcinol has also been proposed for such applications. Both these explosives meet the exacting requirements for a primary explosive in that they may be exploded consistently when required by a small pulse of energy (from a small electric current or mechanical impact, for example) and they are reasonably safe and not easily exploded during manufacture and subsequent handling. However, both explosives suffer from a tendency to be brisant and too violent to ignite satisfactorily a primary or delay train, since an adjacent element in the train tends to be scattered rather than ignited. Attempts have been made to reduce the violence of these explosives by the addition of an inert substance, but this has resulted in an undesirable reduction in the sensitiveness of the explosives.

It is therefore an important object of the present invention to provide primary explosives which are less violent than lead styphnate but in which the desirable sensitiveness to ignition is not significantly impaired. These primary explosives are extremely effective initiators and are found to have good thermal stability which is generally much superior to that of lead styphnate.

A further aim of the invention is to provide primary explosive compositions which have very good igniferous properties and which are particularly effective when applied to an electric bridge wire igniter either as fusehead dips or dry loaded compositions, and when used in conducting compositions devices to ignite pyrotechnics and delay compositions.

Another object of the invention is to provide primary explosive compositions which on ignition evolve gas in a manner rendering them particularly suitable for operating explosive switches or explosive motors.

According to the invention there is provided a new class of primary explosives each of which is a polybasic lead salt of a di- or a tri-nitro-substituted resorcinol and each of which has 3, 4, 5 or 6 atoms of lead per aromatic nucleus. Each polybasic salt has a precise lead content whose value lies between 70% and 80% by weight of the salt.

The preferred lead salts are lead salts of 2:4-dinitroresorcinol, 4:6-dinitroresorcinol, or sym-trinitroresorcinol (styphnic acid), in which there is combined at least two molecular proportions of a base which may be lead oxide or lead hydroxide. We have discovered that the presence of the base in such polybasic lead salts modifies to a desirable extent the violence with which these salts ignite and yet surprisingly does not seriously impair their sensitiveness to ignition as compared with, for example, normal lead styphnate. However, where the combined base increases the overall lead content to more than 80% by weight, both the sensitiveness and explosive power are reduced to an unacceptable extent.

A polybasic lead salt in accordance with the invention may generally be prepared by reacting together at an elevated temperature an aqueous solution of a soluble salt of the appropriate nitro-substituted resorcinol, an aqueous solution of a soluble lead salt and an aqueous solution of an alkali.

The soluble lead salt and the nitro-substituted resorcinol are provided in stoichiometric proportions in accordance with the composition of the lead salt desired provided that sufficient alkali is present. Thus, for example, when this ratio is 4:1 a polybasic salt containing four atoms of lead is produced. Sufficient alkali should be provided to allow the reaction to proceed to completion. The polybasic lead salt is precipitated in a granular form which may be readily and safely isolated and dried to give a free-flowing product suitable for dry-loading purposes.

In accordance with a further feature of the invention, the igniferous properties of these polybasic lead salts may be improved by incorporating into the salts a minor proportion of finely-divided boron, preferably between 5 and 15% by weight. The polybasic lead salts incorporating boron give compositions which are effective in a variety of applications including application to an electric bridgewire by dry loading or fusehead dipping, to conducting composition devices for igniting pyrotechnics and delay compositions, and to operate explosive switches.

We have found that boron may be conveniently incorporated into the polybasic lead salts of the invention by the process described in our U.S. Pat. No. 3,238,076; that is, finely-divided boron is held in a stirred aqueous suspension which also contains a dissolved reactant and the other reactants are added to this suspension to yield a product in which boron is intimately dispersed within the crystals of primary explosive.

German Pat. No. 407416 describes an explosive addition product formed by reacting a slurry of 3 molar proportions of litharge with 1 molar proportion of lead trinitroresorcinate. The product is stated to contain 74.3% lead which approximates to the theoretical 73.99% for $C_6HO_{11}N_3Pb_4$, but we have found that, although the product prepared by the process analyses close to the values stated in German Patent No. 407416, this product is in fact a variable, non-reproducible, mixture of lead salts and that the process does not yield a specific, well-defined polybasic lead salt as provided by the present invention. A further advantage of the present invention is that the reactant solutions may be filtered free from foreign matter such as grit which is very undesirabel in sensitive explosives.

Typical examples in accordance with the invention of the preparation of polybasic lead nitro-substituted resorcinates and boron-containing compositions therewith will now be described.

EXAMPLE 1

An aqueous base solution of disodium styphnate (prepared by adding 0.3 mole sodium carbonate to 0.3 mole styphnic acid in 2 liters of water) is stirred at 80°–90°C and to this solution are added simultaneously 1.60 liters of aqueous lead nitrate solution (containing 1.2 moles lead nitrate) and 1.60 liters sodium hydroxide solution (containing 1.8 moles sodium hydroxide) over a period of 40 minutes. The precipitating temperature is maintained at 80°–90°C during the addition and stirring is discontinued about ten minutes after the addition is complete. The product then settles quickly, and the clear supernatant liquor is decanted hot. The product is washed in the precipating pan by decantation, freed from excess water, washed with methylated spirits and dried either on the hot table at 60°C or by passage of dry air.

340g of a free-flowing orange coloured crystalline product having a bulk density of 0.8 g/ml and a lead content by weight of 72.73% are obtained. [The theoretical yield is 341.1 g from a reaction according to the equation

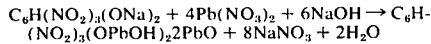

The lead content of $C_6H(NO_2)_3(OPbOH)_22PbO$ is 72.82% by weight.] The ignition temperature of the product is 255°C and it is very suitable for use as a fast burning delay composition and as a less brisant igniter material.

EXAMPLE 2

1.60 liters of aqueous sodium hydroxide solution (containing 3.05 moles sodium hydroxide) and 1.60 liters of aqueous lead acetate solution (containing 1.8 moles lead acetate trihydrate) are added simultaneously during 40 minutes to 2 liters of aqueous disodium styphnate solution (prepared by adding 0.3 moles sodium carbonate to 0.3 moles of styphnic acid). The temperature of the reactant mixture is maintained at 85°C during precipitation. A further 10 minutes stirring after addition is given, and the product settles quickly when the stirring is discontinued to permit ready decantation of the hot supernatant liquor. The product is washed in the precipitating pan by decantation, freed from excess water, washed with methylated spirits and dried either on the hot table at 60°C or by passage of dry air.

475 g of free flowing orange red crystalline material having a bulk density of 1.5 g/ml and a lead content of 78.80% by weight are obtained. [The theoretical yield of lead salt is 474.9 g from a reaction according to the equation

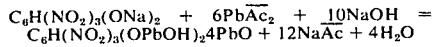

The lead content of $C_6H(NO_2)_3(OPbOH)_24PbO$ is 78.42% by weight.] The product has an ignition temperature of 255°C and is suitable as a delay composition and as a less brisant igniter material.

A similar material may be prepared by the process as described above, but in which the lead acetate is replaced by a similar molar proportion of lead nitrate.

EXAMPLE 3

To 1.20 liters of an aqueous base solution of disodium 4:6-dinitroresorcinate [containing 20 g (0.10 mole) of 4:6-dinitroresorcinol and 10.6 g (0.10 mole) sodium carbonate to give a pH of about 7.45] are added with stirring 150 mls lead nitrate solution [containing 33.13 g (0.10 mole) lead nitrate] during ten minutes. 300 mls lead nitrate solution [containing 66.26 g (0.2 mole) lead nitrate] and 300 mls sodium hydroxide solution [containing 16 g (0.4 mole) sodium hydroxide] are then added during 20 minutes, the temperature of the reactant mixture being maintained at 90°C. Stirring is discontinued ten minutes after the addition is completed, the precipitated product is allowed to settle and, after the mother liquor has been decanted, is washed with water by decantation and dried by passage of dry air or on a hot table maintained at 50°C. The yield of product is 85.87 g having a bulk density of 0.5 g/ml and a lead content of 71.0%. [Expected yield would be 87 g from a reaction according to the equation

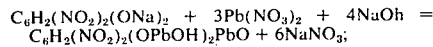

and theoretical lead content of $C_6H_2(NO_2)_2(OPbOH)_2.PbO$ is 71.47%.]

The product has an ignition temperature of 245°C and is very suitable as a delay composition and as an igniter material.

EXAMPLE 4

To 1.2 liters of an aqueous base solution of disodium 4:6-dinitroresorcinate (prepared as in Example 3) are added with stirring 150 mls aqueous lead nitrate solution (containing 33.13g lead nitrate) during ten minutes. 450 mls of aqueous lead nitrate solution [containing 99.39g (0.3 mole) lead nitrate] and 450 mls sodium hydroxide solution [containing 24g (0.6 mole) sodium hydroxide] are then added simultaneously with stirring during 30 minutes. The resulting precipitated product is isolated and dried as in Example 3 to yield 106g of a free-flowing crystalline material having a bulk density of 0.6g/ml and a lead content of 75.80%. [The theoretical yield would be 109g from a reaction according to the equation

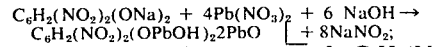

the theoretical lead content of $C_6H_2(NO_2)_2(OPbOH)_22PbO$ is 75.85%]

The product has an ignition temperature of 246°C and is very suitable as a delay composition and as a less brisant igniter material.

EXAMPLE 5

To a stirred aqueous base solution of 1.20 liters of disodium 2:4-dinitroresorcinate [containing 20g (0.1 mole) 2:4 -dinitroresorcinol and 10.6g (0.1 mole) sodium carbonate] are added 150 mls lead nitrate solution [containing 33.13g (0.1 mole) lead nitrate] and 450 mls aqueous sodium hydroxide solution [containing 24g (0.6 mole) sodium hydroxide] are then added simultaneously during 30 minutes, the temperature of the reactant mixture being maintained at 90°C throughout the addition. The resulting precipitated product is isolated and dried as in Example 3 to yield 115g of a free-flowing granular material density of 2.24g/ml and a lead content of 76.0% by weight. [Theoretical yield would be 109g for a reaction according to the equation

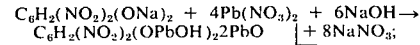

the theoretical lead content of $C_6H_2(NO_2)_2(OPbOH)_22PbO$ is 75.8%]

EXAMPLE 6

The process of Example 5 is repeated except that the volume of each of the simultaneously added aqueous solutions of lead nitrate and sodium hydroxide are increased to 600 mls and that these solutions contain respectively 132.52g (0.4 moles) lead nitrate and 32.0g (0.8 mole) sodium hydroxide. The resulting precipitated product is isolated and dried as in Example 3 to yield 130g of a free-flowing crystalline material having a bulk density of 2.25g/ml and a lead content 77.27% by weight. [The theroretical yield is 131.5g from a reaction according to the equation $$C_6H_2(NO_2)_2(ONa)_2 + 5Pb(NO_3)_3 + 8NaOH$$
$$C_6H_2(NO_2)_2(OPbOH)_23PbO + 10 NaNO_3.$$

and the lead content of $C_6H_2(NO_2)_2(OPbOH)_23PbO$ is 77.27% by weight].

The product has an ignition temperature of 240°C and is very suitable as a delay composition and as a less brisant igniter material.

EXAMPLE 7

A composition consisting of the polybasic lead salt as produced by the process described in Example 1 in which finely-divided boron is incorporated may be prepared as follows.

20g of amorphous boron (particle size about 1.0 micron) are added to 2 liters of a stirred aqueous solution, containing 0.3 moles of disodium styphnate, heated at 85°C. 1.60 lites of aqueous lead nitrate solution (containing 1.2 moles lead nitrate) and 1.60 liters of sodium hydroxide solution (containing 1.8 moles of sodium hydroxide) are added simultaneously during 40 minutes, while the precipitating temperature is maintained at 85°C. The stirring is continued for a further 15 minutes after addition. The boron is completely incorporated within the lead styphnate crystals which latter settle readily when the stirring is discontinued. The clear supernatant liquor is decanted hot and the product is washed in the precipitating pan by decantation. The product is freed from excess water, washed with methylated spirits and dried on the hot table at 60°C or by passage of dry air. The yield of product obtained is 360 gms having a boron content 5.5 per cent by weight and lead contant 65.18 per cent by weight. The ignition temperature of the material is 250°C and it is suitable as an efficient electric igniter material for dry loading or as a fuse head paste ingredient in an ethyl cellulose base to give fuseheads having very good thermal stability.

EXAMPLE 8

A composition consisting of the polybasic lead salt as produced by the process described in Example 2 in which finely-divided boron is incorporated may be prepared as follows.

25g of amorphous boron (average particle size about 1.0 micron) are added to 2 liters of a stirred aqueous solution, containing 0.3 moles disodium styphnate, heated at 85°C. 1.60 liters of aqueous lead nitrate solution (containing 1.8 moles lead nitrate) and 1.60 liters of sodium hydroxide solution (containing 3.05 moles sodium hydroxide) added simultaneously during 40 minutes while the temperature is maintained at 85°C. Stirring is discontinued ten minutes after the addition is complete and the precipitated product, which incorporates all the boron added, is isolated and dried as in Example 7 to yield 500g of a free flowing material having a bulk density of 1.0g/ml and containing 5% by weight of boron. The product has an ignition temperature of 255°C and may be used as a thermally stable igniter material for dry loading onto electric bridgewires or as a fusehead dip, particularly with an ethyl cellulose base.

EXAMPLE 9

A composition consisting of the polybasic lead salt as produced by the process described in Example 3 in which finely-divided boron is incorporated may be prepared as follows.

6g boron (average particle size about 1.0 micron) are suspended in a stirred aqueous solution of disodium 4:6-dinitroresorcinate (0.1 mole) heated at 85°C. The procedure is then carried out as described in Example 3 to yield 90g of the free flowing material having an ignition temperature of 245°C, and containing by weight 6.3% boron and 66.5% lead. This material is useful as a thermally stable igniter material for electric bridgewire applications, either dry-loaded or as a fuse-head dip.

EXAMPLE 10

A composition consisting of the polybasic lead salt as produced by the process described in Example 4, in which finely-divided boron is incorporated may be prepared as follows.

6 g boron (average particle size about 1.0 micron) are suspended in a stirred aqueous solution of disodium 4:6-dinitrosocinate (0.1 mole) heated at 85°C. The procedure is then carried out as described in Example 4 to yield 110 g of a free flowing material having an ignition temperature of 245°C, and containing by weight 5.2% boron and 70.6% lead. This material is useful as a thermally stable igniter material for electrical bridgewire applications, either dry-loaded or as a fuse-head dip.

The desirable reduction in the violence of the polybasic lead salts provided by the invention, as compared with the previously known normal and monobasic lead styphates, may be demonstrated by igniting a known quantity of each of the lead salts under standardised conditions in a closed chamber of known volume and measuring the pressure of gas produced during the period of the ignition, which is generally complete within about 20 milliseconds. The more violent the ignition the more rapidly is the maximum gas pressure attained and the higher is the value of this maximum pressure. The values obtained by igniting 16 mg samples in a closed chamber of 1 ml volume are as follows.

| Sample | Maximum pressure lbs/sq. in. | Time to attain maximum (milliseconds) |
|---|---|---|
| Normal lead styphnate | 1,400 | less than 0.1 |
| Monobasic lead styphnate | 1,100 | less than 0.1 |
| Polybasic lead styphnate | 200 | 0.5 |

The reduction in violence of the polybasic lead salt which was prepared by the process described in Example 3 is clearly apparent.

The fact that the same polybasic lead salt does not suffer a significant reduction in sensitivity as compared with the normal and monobasic lead styphates can be seen from comparison of the Figures of insensitiveness as measured by the standard Rotter Machine.

| Sample | Figure of Insensitiveness |
|---|---|
| Normal lead styphnate | 25 |

| Sample | Figure of Insensitiveness |
|---|---|
| Monobasic lead styphnate | 10 |
| Polybasic lead styphnate | 10.5 |

In addition, thermal stability measurements show that the polybasic lead salt is unchanged even after heating for 2 hours at 170°C, whereas normal lead styphnate decomposes at 130°C.

The invention includes, as one of its aspects, compounds consisting essentially of a lead salt of di- or tri-nitro-resorcinol of the formula

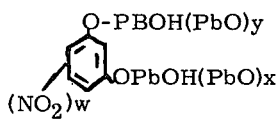

wherein
$w$ is 2 or 3, $x$ is 1 or 2, and
$y$ is 0, 1 or 2.

We claim:
1. A polybasic lead salt of a di- or a tri-nitro-substituted resorcinol containing 3, 4, 5 or 6 atoms of lead per aromatic nucleus.
2. A polybasic lead salt according to claim 1 in which the nitro-substituted resorcinol is 2:4-dinitroresorcinol, 4:6-dinitroresorcinol or sym-trinitroresorcinol.
3. A polybasic lead salt according to claim 2 in which the nitro-substituted resorcinol is combined with at least two molecular proportions of lead oxide or lead hydroxide.
4. A compound consisting essentially of a lead salt of di- or tri-nitro-resorcinol of the formula

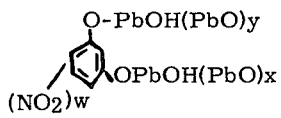

wherein
$w$ is 2 or 3, $x$ is 1 or 2 and
$y$ is 0, 1 or 2.

* * * * *